United States Patent [19]

Leuenberger et al.

[11] Patent Number: 4,619,527
[45] Date of Patent: Oct. 28, 1986

[54] PROCESS AND DEVICE FOR AUTOMATICALLY DETECTING FAULTS IN FABRICS AND SIMILAR TEXTILE SHEET-LIKE STRUCTURES

[75] Inventors: Rolf Leuenberger, Pfäffikon; Christian Hunziker, Mönchaltorf, both of Switzerland

[73] Assignee: Zellweger Uster, Ltd., Uster, Switzerland

[21] Appl. No.: 559,802

[22] Filed: Dec. 9, 1983

[30] Foreign Application Priority Data

Feb. 3, 1983 [CH] Switzerland .................... 624/83

[51] Int. Cl.$^4$ .................... G06K 9/08; G01N 21/16; G01N 21/32
[52] U.S. Cl. .................... 356/238; 356/232; 356/430; 356/390
[58] Field of Search ............ 356/237, 238, 229, 232, 356/430, 431, 388, 390, 391

[56] References Cited

U.S. PATENT DOCUMENTS 3,658,420 4/1972 Axelrod ........................ 356/71

OTHER PUBLICATIONS

G. L. Rogers, "Non–Coherent Optical Processing", John Wiley, New York, 1977, S. H. Lee, Editor.

"Optical Information Processing", Topics in Applied Physics, Springer, vol. 23 and 48.
M. A. Monahan et al., in IEEE Proceedings, vol. 65 (1977), pp. 121–129.
A. Rosenfeld and A. C. Kak, "Digital Picture Processing", Academic Press, New York, 1976.
W. K. Pratt, "Digital Image Processing", John Wiley & Sons, New York, 1978.
W. Frei and Chung–Ching Chen, in IEEE Transactions on Computers, Oct. 1977, "Fast Boundry Detection".

*Primary Examiner*—John E. Kittle
*Attorney, Agent, or Firm*—Antonelli, Terry & Wands

[57] ABSTRACT

A boundary or line-detecting process using image-filtering is used to detect fabric faults in moving textile fabric webs. A double-slit mask or an electrical equivalent thereof is used as a filter. The output signal of the filter is formed from the difference between the two luminosity values averaged across each slit of the filter mask. The image-filtering system is realized either by noncoherent optical spatial filters or by means of digital electronic circuits. The surface of the fabric web generally has a certain texture which already contains boundary and line elements. These basic values are used to derive fabric-specific parameters from which the boundary or line elements due to fabric faults are deducted. The boundary or line elements which remain, owing to their increased contrast, unambiguously indicate faults in the fabric web.

20 Claims, 13 Drawing Figures

PROCESS AND DEVICE FOR AUTOMATICALLY DETECTING FAULTS IN FABRICS AND SIMILAR TEXTILE SHEET-LIKE STRUCTURES

BACKGROUND OF THE INVENTION

The present invention relates to a process and a device for automatically detecting faults in fabrics and similar textile sheet-like structures by filtering an image to increase the contrast between the overall texture of the article perceived as normal and the local deviations therefrom perceived as faults.

There are already various existing processes in which the surface of the material is scanned either by means of moving light spots or using sensors arranged in series. The luminosity values produced by the optico-electrical signal converters used in these processes may be prefiltered and are then passed to a threshold value stage, ideally after averaging, because it is found that in particular in the case of fabrics, averaging the luminosity values over several individual threads has the effect of increasing the signal to noise ratio and hence of securing significant benefits for the subsequent signal-processing stage.

In the existing processes, the luminosity values are averaged as a result of the shape and size of the scanned or illuminated area or of the individual sensor. In many cases, two scanning systems are operated in parallel in such a way that one has horizontal averaging characteristics and the other has vertical averaging characteristics, the directions of the averaging characteristics corresponding to the directions of the warp and weft threads in the fabric. There are also existing automatic fabric inspection processes in which the luminosity distribution of the fabric surface is analyzed by means of coherent optical Fourier transformation.

SUMMARY OF THE INVENTION

The present invention relates to such a process and such a device for automatically detecting faults in fabrics and similar textile sheet-like structures by filtering an image to increase the contrast between the overall texture of the article perceived as normal and local deviations therefrom perceived as faults.

One characteristic feature of the process according to the present invention is that faults in the fabric web are detected by means of their boundaries or lines. It should be mentioned at this point that the human eye, which has to be taken into account as a comparison in assessing fabric faults, also has a specific sensitivity for boundaries or lines (so-called phase sensitivity).

The process for detecting boundary or line elements calls for the image of the fabric surface to be processed in two dimensions, i.e., to be filtered. Such image-filtering can be effected by means of a double-slot mask and can be realized in two principally different ways:

1. By non-coherent optical filtering as disclosed in other areas of application. These processes have been publicized in, for example: G. L. Rodgers, "Non-Coherent Optical Processing", John Wiley, New York, 1977; S. H. Lee, Editor, "Optical Information Processing", Topics in Applied Physics, Springer, Vol. 23 and 48; and M. A. Monahan et al, in IEEE Proceedings, Vol. 65 (1977) pp. 121-129. It is a significant disadvantage of conventional non-coherent optical filtering that, in general, negative weightings in the mask function cannot be solved completely. However, the simplicity of the proposed filter mask permits weighting with the correct sign by means of separate sensors in accordance with one feature of the present invention.

2. The trend has been in recent years to digital image processing, where suitable components are available in the form of inexpensive fast processors and CCD sensors. Digital image processing is flexible, accurate and robust, since mechanical scanners are not required. This so-called digital spatial filtering has been disclosed in A. Rosenfeld and A. C. Kak, "Digital Picture Processing", Academic Press, New York, 1976; W. K. Pratt, "Digital Image Processing", John Wiley & Sons, New York, 1978; W. Frei and Chung-Ching Chen, in IEEE Transactions on Computers, Oct. 1977: "Fast Boundary Detection".

Even the normal, faultless surface structure of a textile fabric web can be composed of line and boundary elements. The boundary-detection processes, therefore, continuously produce output values from which average, fabric-specific reference quantities can be formed to serve as a measure of the normal surface structure.

Boundary or line elements of faults in the fabric web, however, differ significantly in their dimensions and/or degree of contrast from the surface structure. A continuous comparison of the boundary and line elements found with said fabric-specific reference standards enables the faults in the fabric web to be detected in a reliable manner.

The considerable boundary and line sensitivity of suitable boundary-detecting processes and their insensitivity to other textural elements (for example, graininess) permit the detection of fabric faults of the size of individual threads, even if the filter system itself has an inferior resolution. The resolution of the filter system is reduced to such an extent that interfering signals due to high spatial frequencies are suppressed. This way of lowering the resolution, which can be referred to as optical low-pass filtering, makes it possible to cut the number of sensor elements used when realizing the system in digital electronics hardware and can, therefore, lead to particularly-economical solutions.

It is a particular advantage of the boundary-detecting processes that it is possible to make selective distinctions between the boundary and line elements according to their direction and length, since direction and sensitivity of the filters can be determined by a suitable choice of filter masks. It is advisable, as a rule, to operate various filter stages in parallel, yet which arrangement, if realized in digital electronics hardware, only requires a single invariable sensor system. In this case, the characteristics of the filters can be very flexibly determined by electronic circuits or programming. The process according to the invention is, therefore, particularly suitable for the application of modern technologies using fast processors.

The image-filtering and threshold value formation system employed in the process according to the invention involves, in essence, first of all analyzing the continuously-incoming boundary or line elements for significant departures from the normal fabric structure. So long as no such boundary or line elements are found, said processes produce no signals. Only when marked boundary or line elements occur are the corresponding signals stored and analyzed in a processor connected therebehind.

The result of this analysis will show faults in the fabric web. Since the occurrence of faults in the fabric web can be regarded as a statistically-rare event, the processor connected downstream has a sufficiently-long time interval available to allow the analysis to proceed at a speed for which a relatively-slow and correspondingly-inexpensive processor is adequate.

These and other objects, features and advantages of the present invention will become more apparent from the following detailed description of various preferred embodiments.

BRIEF DESCRIPTION OF THE DRAWINGS

The process and a device will now be illustrated in the form of examples with reference to the description and the figures, of which

DETAILED DESCRIPTION OF THE PREFERRED EMBODIMENTS

Figure 1:
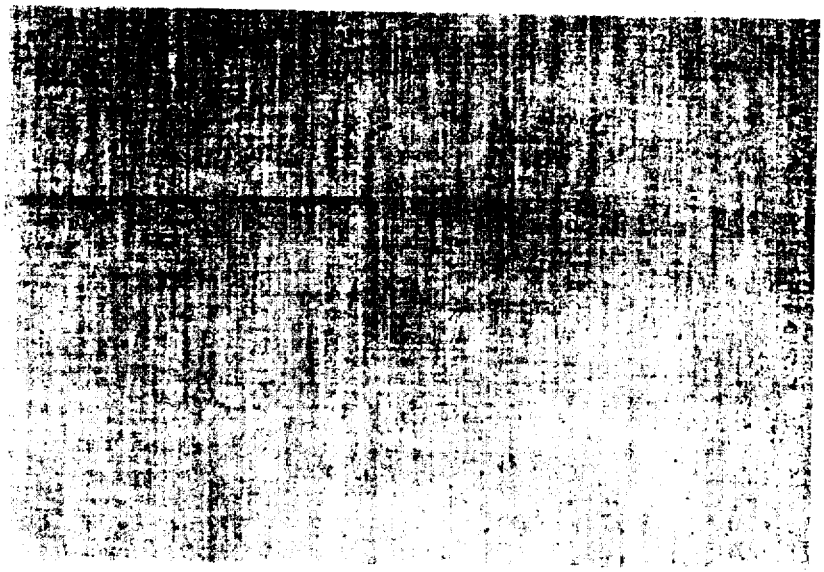
FIG. 1 shows a photographic reproduction of a piece of fabric.
Figure 2:
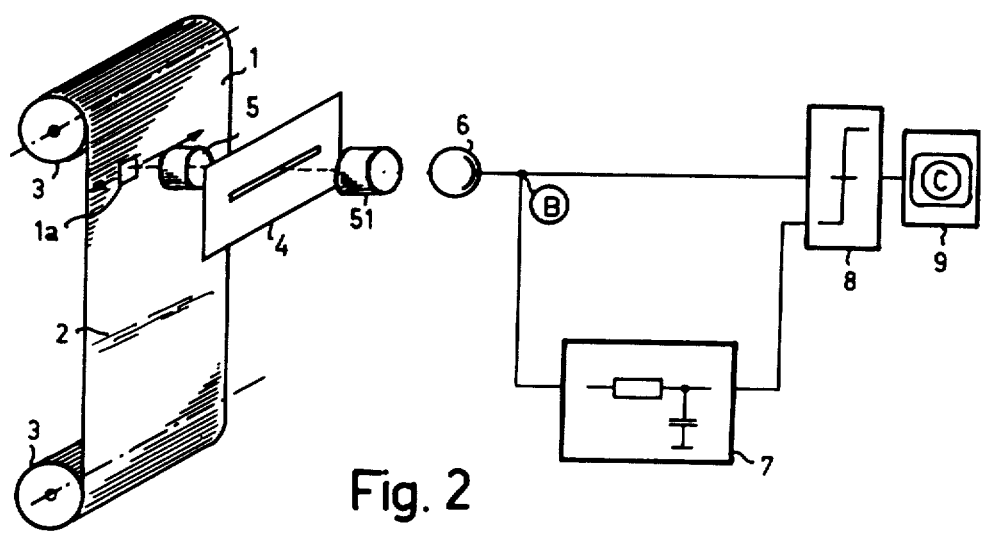
FIG. 2 shows an optical spatial filter with a simple slit diaphragm.

FIG. 1 depicts a section of a fabric web 1 having a fabric fault 2. FIG. 2 shows the fabric web 1 diagrammatically as it runs on an unrolling and rolling-up mechanism 3. At a right angle to the fabric web is an optical scanner 5 which scans the fabric web 1 line by line and forms an image on the filter mask 4 in the form of a momentary section 1a of the fabric web 1. The luminosity values produced at the filter mask 4 are transformed, via an optical integrator 51 and by means of a photoelectric converter 6, into electrical signals at point B which can produce a grey value image as shown in FIG. 3.

Figure 3:
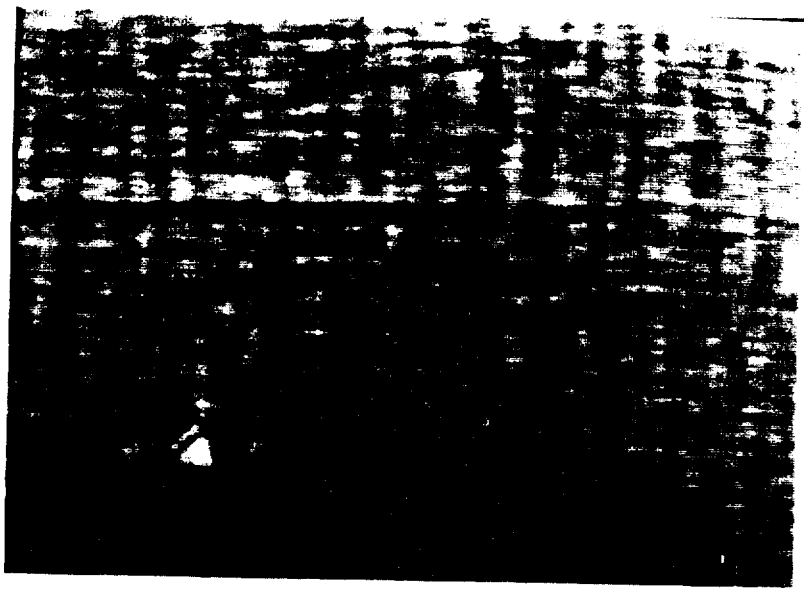
FIG. 3 shows a grey value image of a fabric fault, which has been obtained with a simple slit diaphragm.

If these signals produced by the converter 6 at point B are then applied to a threshold value stage 8, on the one hand directly, and on the other hand, via a low-pass filter 7; and if the output of the stage 8 is applied to a first monitor 9, a black and white picture (FIG. 4) which corresponds to the grey value image shown in FIG. 3 will appear on the monitor's screen C. However, the realiability of this type of fabric fault detection is still inadequate in some respects, since it will also depict as faults area elements of the fabric web whose texture differs only insignificantly from the surrounding texture. The effect of the filter mask 4 with one slit is the same as that of the known processes already mentioned as averaging luminosity values over several individual threads.

Figure 5:
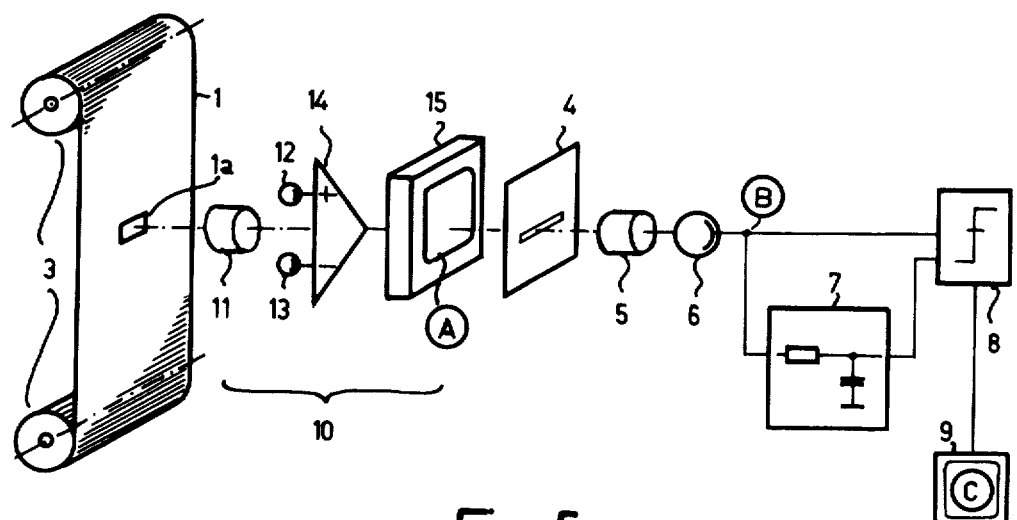
FIG. 5 shows an optical spatial filter as shown in FIG. 2, with an intermediate-connected difference stage.
Figure 6:
FIG. 6 shows an image which is of a fabric structure and which has been derived from the signal flux of FIG. 5.
Figure 7:
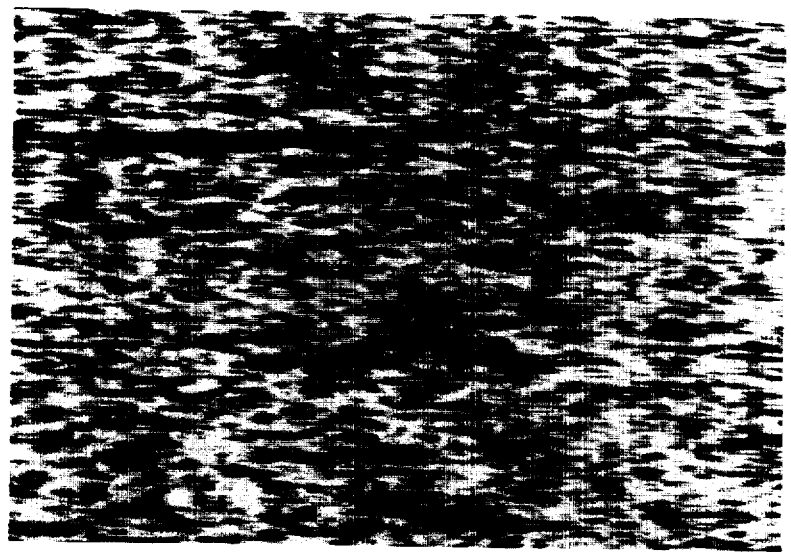
FIG. 7 shows a further image of a fabric structure after passing through the spatial filter of FIG. 5.

If now, as seen in FIG. 5, a prestage comprising an optical scanner 11, two optico-electrical converters 12, 13 which have outputs applied to respective inputs of a difference amplifier 14, and a further monitor 15 is arranged between the filter mask 4 and the fabric web 1, and the filter mask 4 is directed—not directly at the fabric web 1—but at the picture A of the further monitor 15, the detection reliability in the resulting black-white picture can be increased considerably. This increase in detection reliability in the resulting black-white picture is demonstrated by FIGS. 6 and 7. FIG. 6 is the representation of a fabric section as it appears on the screen A of the further monitor 15 (FIG. 5). FIG. 7 shows the same fabric section in the image obtained from a signal at connection point B of the arrangement shown in FIG. 5.

Figure 8:
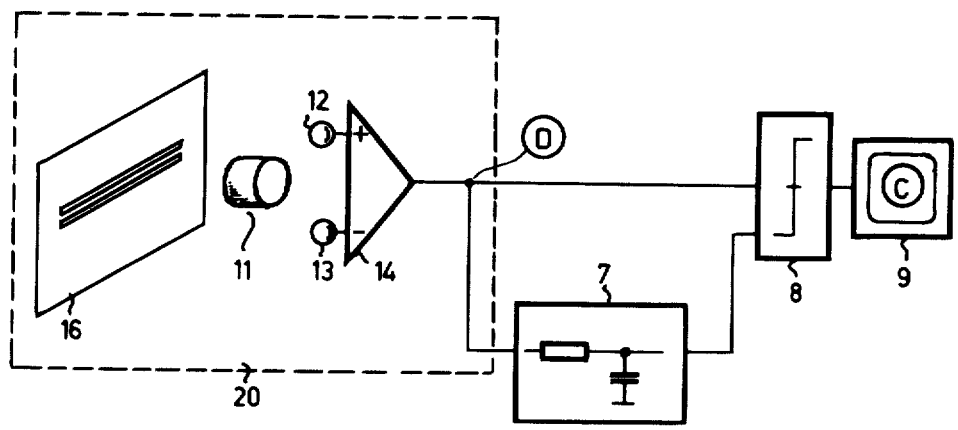
FIG. 8 shows an optical spatial filter with a double-slit diaphragm.

Now, the arrangement in FIG. 5 can be considerably simplified, as shown in FIG. 8, by applying the output of the difference amplifier 14 to the threshold value stage 8 directly and through the low-pass filter 7. A double-slit diaphragm 16 is inserted, as a mask, between the fabric web 1 and the optical scanner 11 to scan the fabric web 1 in the form of two parallel image lines from which the differences in the luminosity values and their weighting are obtained. This arrangement of the double-slit diaphragm as filter mask 16, optical scanner 11, optico-electrical converts 12, 13, and difference amplifier 14 comprises an optical spatial filter 20.

Figure 4:
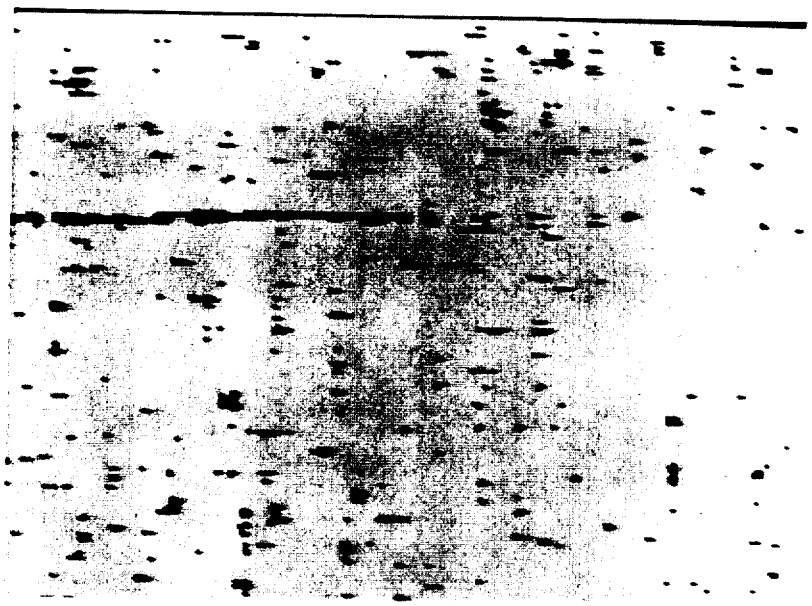
FIG. 4 shows a black-white image derived from the grey value image of FIG. 3.
Figure 9:
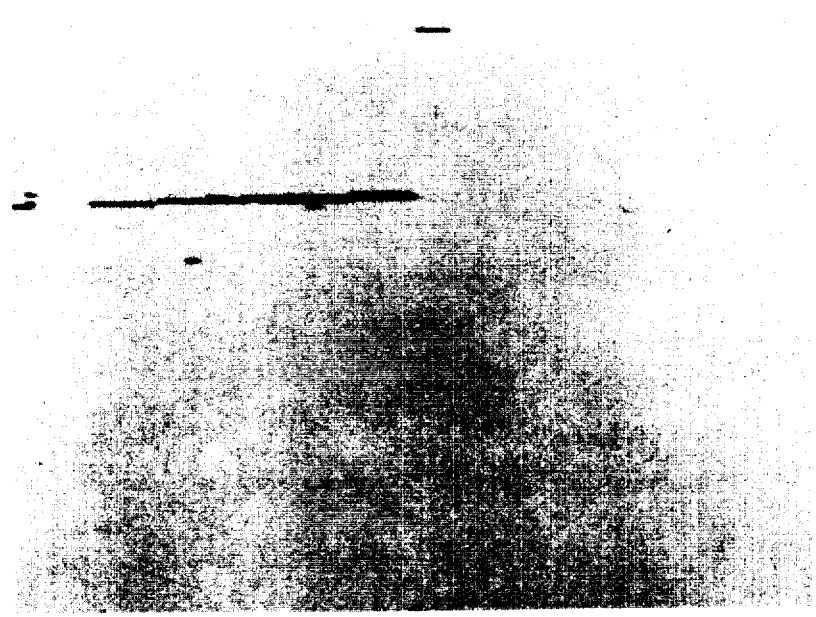
FIG. 9 shows a black-white image of a fabric fault, which has been obtained by means of a double-slit diaphragm as shown in FIG. 8.

FIG. 9 shows, on screen C of monitor 9, a fabric fault 2 in a black-white picture obtained by means of this double-slit diaphragm 16. As can be seen, the further increase in detection reliability compared with the picture shown in FIG. 4 is considerable.

Figure 10:
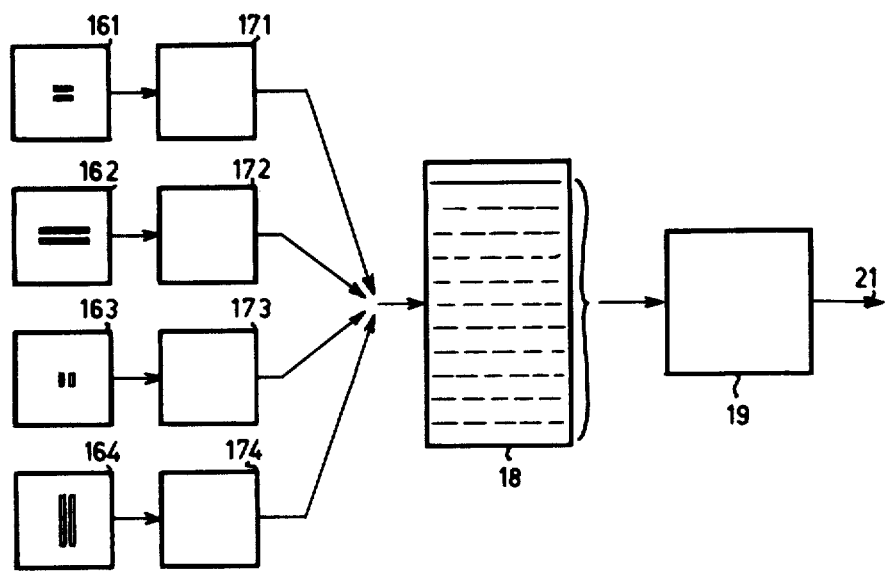
FIG. 10 shows a multichannel image-processing system for total detection of all fabric faults with horizontal and vertical components.

In order to detect fabric faults of any type, it is preferable to operate several filter stages in parallel, the individual stages differing in the provision of slits in the filter mask which are different in terms of their length and orientation. An example of this is shown in FIG. 10, where schematically, two horizontally oriented and two vertically oriented double-slit diaphragms 161, 162, 163, 164 have been provided as filter masks of which two have a short double-slit and the other two have a long double-slit. The short double-slits 161, 163 only cover a small piece of the fabric surface and, in so doing, find the local deviations therein, while the long double-slits 162, 164 are used for forming the average from the luminosity values of a larger portion of the fabric surface. The downstream preprocessing stages 171, 172, 173 and 174 essentially contain the components shown in FIG. 8, such as optical scanner 11, converters 12 and 13, difference amplifier 14, low-pass filter 7 and threshold value stage 8. The outputs of these preprocessing stages are connected to a matrix 18 on which all the points of that section of the fabric web 1 processed last and which are potentially part of a fabric fault are stored in the form of a table. The matrix 18 may be implemented in the form of a random access memory (RAM). A subsequent process which takes place in stage 19 analyzes the data stored in the matrix 18 and issues fault indications in the form of a fault signal 21 which may be viewed on a monitor 9, as already described. The stage 19 may take the form of a conventional microprocessor programmed to analyze the stored data in accordance with a standard process.

Figure 11:
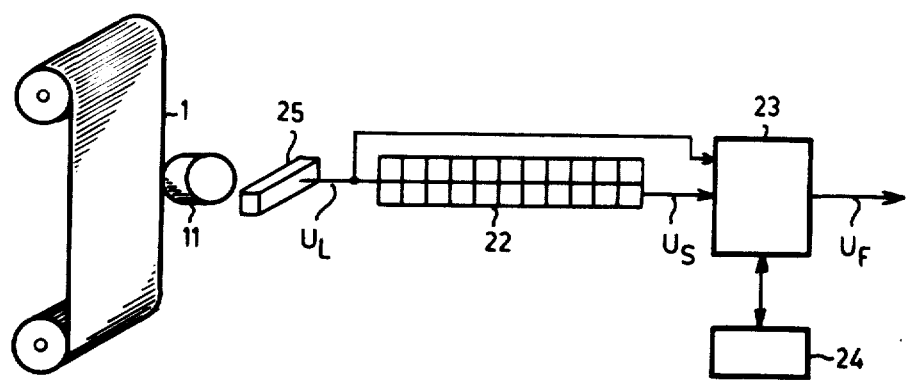
FIG. 11 shows a diagram of a digital image-filtering arrangement.

An image-filtering system comprising the filter masks proposed can be electronically realized in the form of, for example, an arrangement as seen in FIG. 11. The fabric web 1 is imaged by an optical scanner 11 onto a line sensor 25. At the output of this line sensor 25 there is available an electrical signal $U_L$ which is proportional to the luminosity values of the fabric line imaged at the moment. A 2-line memory 22, which can be provided as a shift register, for example, can be used to store whichever two lines have been scanned last. Signal $U_L$ and memory content $U_S$ are applied to a filter processor 23 whose output $U_F$, like the output signal from the optical filters, is applied to a threshold value stage in the manner shown in FIG. 8, for example. In addition, an intermediate memory 24 may be assigned to the filter processor 23, when the processor 23 is provided as a standard microcomputer.

Figure 12:
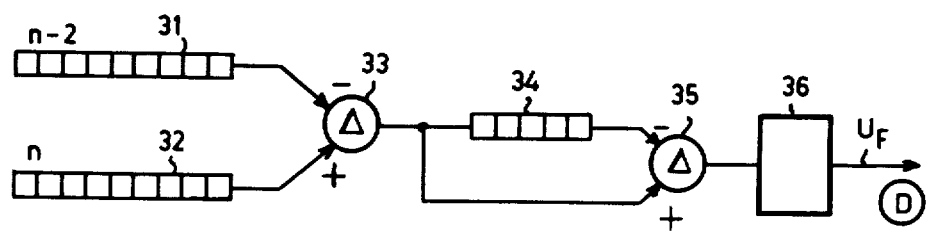
FIG. 12 shows an example of a digital realization of a horizontal filter mask.

FIG. 12 shows a possible electronic realization of a horizontal double-slit filter mask and also shows another possible form of the filter processor 23 in FIG. 11. The values $U_S$ of a scanned line n-2 stored in register 31 from a two-line memory 22, as provided in FIG. 11, are subtracted, at a first difference stage 33, from the values $U_L$ of the current scanning line n stored in register 32. In a further shift register 34, whose number of stages k determines the length of the slit in the filter mask 16, the scanning values are delayed, so that afterwards any scanned value can be subtracted in a second difference stage 35 from its kth predecessor. Continuous summation of the difference values in a summation stage 36 produces the filter output signal $U_F$. This filter output signal $U_F$ is applied, for example, to the connection point D shown in FIG. 8.

Figure 13:
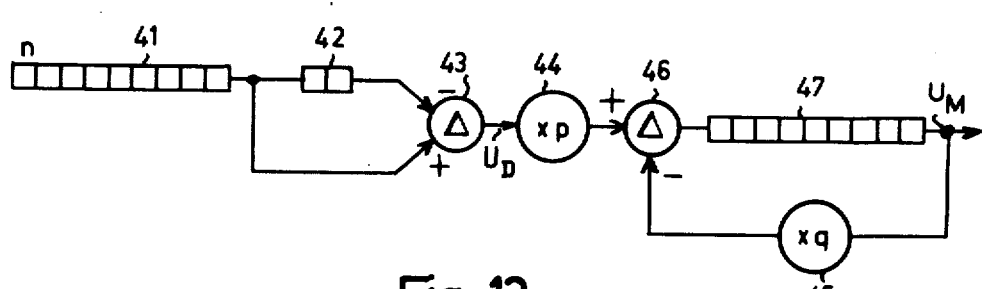
FIG. 13 shows an example of a digital realization of a vertical filter mask.

The electronic realization of a vertical double-slit filter mask preferably takes the form of an arrangement as shown in FIG. 13. This arrangement only requires the current scanning line n which is received from line sensor 25 and stored in shift register 41. A relative shift of the scanned values by two places is obtained by means of a third shift register 42. The signal difference $U_D$ between the current and the penultimate scanned point is available at the output of a third difference stage 43. A running average signal $U_M$ is formed for every scanned point in a conventional manner by means of multipliers 44 (factor p) and 45 (factor q), a fourth difference stage 46 and a fourth shift register 47 having the length of a scanned line n. The choice of factors p and q determines the length of the double-slit mask realized in this way. This recursive signal treatment is a good approximation to averaging at a right angle to the scanning direction and avoids large memory areas having to be constructed for generating or reforming long vertical slit masks, such as in the case where a microcomputer is used for signal processing.

While we have shown and described several embodiments in accordance with the present invention, it is understood that the same is not limited thereto but is susceptible of numerous changes and modifications as known to a person skilled in the art, and we therefore do not wish to be limited to the details shown and described herein but intend to cover all such changes and modifications as are obvious to one of ordinary skill in the art.

What is claimed is:

1. A process for automatically detecting faults in articles, such as fabrics and similar textile sheet-like structures, by filtering an image of the article to increase the contrast between the overall texture of the article perceived as normal and the local deviations therefrom which are perceived as faults, comprising the steps of:
   scanning the surface of the article to form an image of the surface thereof;
   transforming said image using at least two spatial filters which are adapted to detect straight-line contour elements in the weft and warp directions thereof to produce respective transformed images; and
   reducing said transformed images to binary black-white images by comparing them to a characteristic grey value threshold for each direction.

2. A process according to claim 1, further including forming said grey value threshold for each direction by low-pass filtering said respective transformed images.

3. A process according to claim 1, in which the spatial filters used for transforming said image each include a mask which contains two parallel rectangular zones of which one represents a positive weighting and the other represents a negative weighting, and all of the areas of the mask which are outside of the two parallel zones have a zero weighting.

4. A process according to claim 3, in which the mask in the spatial filters used for transforming said image each are formed such that, summed over the entire spatial filter, the products formed by multiplying area elements with the associated weight total zero.

5. A processing according to claim 3, in which the mask in the spatial filters used for transforming said image each are formed such that, summed along any section at a right angle to the two parallel zones, the products of area elements and associated weight total zero.

6. A process according to claim 3, in which the mask in the spatial filters used for transforming said image each are formed such that the weight per unit area element within the individual zones of the filter is constant.

7. A process according to claim 3, in which the two parallel zones of the respective spatial filter masks are aligned in the warp direction and the weft direction, respectively.

8. A process according to claim 3, in which the lengths of the two parallel zones of the respective spatial filter masks are equal to the length of the textural deviations to be detected.

9. A process according to claim 3, in which the widths of the two parallel zones of the respective spatial filter masks are equal to several thread widths.

10. A device for automatically detecting faults in articles, such as fabrics and similar sheet-like structures, by filtering an image of the article to increase the contrast between the overall texture of the article perceived as normal and the local deviations therefrom which are perceived as faults, comprising
    means for optically scanning the surface of the article to form an image of the surface thereof;
    transforming means including least two spatial filters positioned to receive said image from said scanning means for detecting straight-line contour elements in the weft and warp directions of the article to produce first and second electrical signals representing respective transformed images of the scanned surface of the article;
    processing means connected to said transforming means for processing said first and second signals by comparing them to characteristic grey value thresholds to thereby produce a fault signal; and means connected to receive said fault signal for producing a black-white image indicating faults in said article.

11. A device according to claim 10, wherein said transforming means comprises a non-coherent optical filtering arrangement in which each spatial filter includes a spatial filter mask containing two parallel rectangular zones of which one zone represents a positive weighting and the other zone represents a negative weighting, and all of the areas of the mask which are outside of the two parallel zones have a zero weighting.

12. A device according to claim 11, wherein each spatial filter further includes two optico-electrical converters positioned to receive light from only a respective one of the two parallel zones in the spatial filter mask and means for subtracting the output of the converter receiving light from the negatively-weighted zone of said spatial filter mask from the output of the converter receiving light from the positively-weighted zone thereof, the outputs of said subtracting means in said spatial filters forming said first and second signals, respectively.

13. A device according to claim 10, wherein said processing means includes means for generating a signal representing said characteristic grey value threshold from the output of said transforming means.

14. A device according to claim 13, wherein said generating means comprises a low pass filter.

15. A device according to claim 10, wherein said means for optically scanning the surface of the article comprises a line scanner for scanning successive lines on the article in one of the directions of the warp and weft and a line sensor for generating signals representing successive scanned lines.

16. A device according to claim 15, wherein said transforming means comprises storage means connected to the output of said line sensor for storing signals relating to plural scanned lines of the article for a predetermined time, means for comparing the output of said storage means to the output of said line sensor, means for correlating the current output of said comparing means to a previous output of said comparing means, and means for summing the output of said correlating means.

17. A device according to claim 16, wherein said storage means comprises a shift register connected to said line sensor and capable of storing signals relating to two scanned lines on said article.

18. A device according to claim 17, wherein said comparing means comprises a first subtractor for subtracting the output of said shift register from the output of said line sensor and said correlating means comprises a further shift register connected to the output of said first subtractor and a second subtractor for subtracting the output of said further shift register from the output of said first subtractor.

19. A device according to claim 16, wherein said processing means includes means for generating a signal representing said characteristic grey value threshold from the output of said transforming means.

20. A device according to claim 19, wherein said generating means comprises a low pass filter.

* * * * *